United States Patent [19]  [11]  4,448,972
Pfeiffer  [45]  May 15, 1984

[54] ADAMANTYL CONTAINING INTERMEDIATES

[75] Inventor: Francis R. Pfeiffer, Cinnaminson, N.J.

[73] Assignee: SmithKline Beckman Corporation, Philadelphia, Pa.

[21] Appl. No.: 471,112

[22] Filed: Mar. 1, 1983

Related U.S. Application Data

[62] Division of Ser. No. 350,975, Feb. 22, 1982, Pat. No. 4,387,049.

[51] Int. Cl.$^3$ ............................................. C07D 207/16
[52] U.S. Cl. ............................... 548/528; 260/112.5 R
[58] Field of Search .......................................... 548/528

[56] References Cited

U.S. PATENT DOCUMENTS 3,625,985  12/1971  Krimmel ............................. 548/528
4,061,774  12/1977  Chakrabarti et al. ............... 548/528

Primary Examiner—Mary C. Lee
Attorney, Agent, or Firm—William H. Edgerton; Richard D. Foggio; Alan D. Lourie

[57] ABSTRACT

A group of adamantyl containing intermediates is useful to prepare certain oligopeptides which improve kidney function. A representative species of this group is N-(1-adamantyl)-ethanoylproline.

2 Claims, No Drawings

ADAMANTYL CONTAINING INTERMEDIATES

This is a divisional application of U.S. Ser. No. 350,975 filed Feb. 22, 1982, now U.S. Pat. No. 4,387,049.

This invention comprises a new group of chemical compounds whose structures have a prolyl-phenylalanine nuclear skeleton with a characterizing adamantyl-lower alkanoyl substituent on the N-member of the prolyl ring. The utility of the compounds is to improve kidney function and thereby to lower abnormal blood pressure if present.

DESCRIPTION OF THE ART

Belgian Pat. No. 830,911 describes a series of prolyl-phenylalanyl-arginine tripeptides having a ω-phenyl-propionyl at the proline ring nitrogen and an aromatic substituent at the other terminal amino group which are useful in certain analytical procedures. Certain tripeptides alleged to have bradykinin inhibitory activity including prolyl-phenylalanyl-arginine chains are described in PCT specification I.P. No. W080/00252. DT No. 2,943,582 discloses a number of prolyl-phenylalanyl-arginine tripeptides as the naphthyl esters useful as substrates for various enzymes. The present invention is comprised of compounds whose structures differ from those in the prior art as well as from those of my prior inventions in the critical adamantyl-alkanoyl substituent.

DESCRIPTION OF THE INVENTION

The new chemical compounds of this invention have structures which are distinguished by having a prolyl-α-lower alkylphenylalanine dipeptide chain substituted at the ring N-member of the proline ring with a 1-adamantyl alkanoyl group and at the carboxy terminus via the amino group of the alanylamide structure with α-carboxy-ω-guanidinobutyl, ω-guanidino-alkyl, ω-aminoalkyl or ω-carboxyalkyl fragments. The critical structural feature of these compounds is the 1-adamantyl-lower alkanoyl portion of the compounds. The adamantyl group is systematically named tricyclo(3.3.1.1$^{3.7}$)decanyl. Said adamantyl group may also have a hydroxy substituent at the methylene or bridgehead carbon member.

Exemplary of the compounds of this invention are those represented by Formula I:

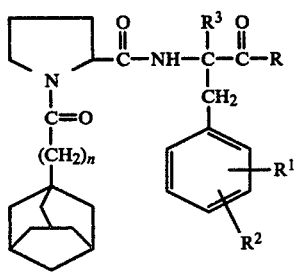

in which:
R is

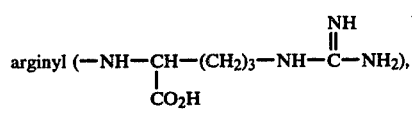

arginyl (—NH—CH(CO$_2$H)—(CH$_2$)$_3$—NH—C(=NH)—NH$_2$),

ω-guanidinoalkylamino (—NH—(CH$_2$)$_m$—NH—C(=NH)—NH$_2$)

ω-aminoalkylamino (—NH—(CH$_2$)$_m$—NH$_2$) or
ω-carboxyalkylamino (—NH—(CH$_2$)$_m$—CO$_2$H);

R$^1$ or R$^2$ each represent hydrogen, methoxy or hydroxy;

R$^3$ is hydrogen or lower alkyl of 1–3 carbons especially methyl;

n is an integer from 1–3; and m is an integer of from 2–6.

A subgeneric group of new compounds of this invention are those of Formula I in which R is arginyl. A second group are those in which R is arginyl, R$^1$ and R$^2$ are each hydroxy or methoxy and n is 1. As stated above R$^3$ is preferably methyl and n is 1.

Also included in this invention are the pharmaceutically acceptable acid addition or alkali metal salts of the compounds of Formula I. Examples of these are the salts prepared by reacting the peptide bases with suitable acids, for example hydrochloric acid, sulfuric acid, sulfamic acid, phosphoric acid, acetic acid, maleic acid, methane sulfonic acid or hydrobromic acid together with the sodium, potassium or calcium salts if a peptide acid is reacted with a base or metal. Such salts are prepared by methods known to the art.

The compounds of this invention are prepared by a reaction sequence which involves, as a key step, formation of the amide group present between the prolyl fragment and the α-alkylphenylalanyl fragment using standard peptide coupling methods. The overall sequence of peptide formation can also be reversed which sequence may even be preferred if R in Formula I contains a basic or acid center rather than a protected group.

Reaction Sequence A

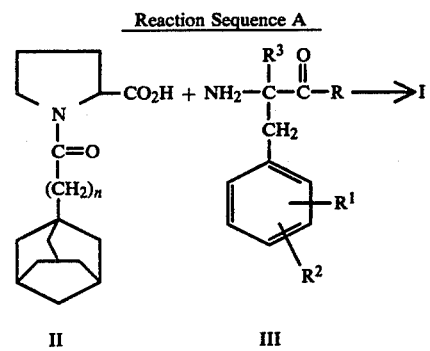

In Reaction Sequence A, the symbols are as described above or protected versions thereof.

In the formation of the amide bond in Reaction Sequence A, standard peptide coupling methods are used. Especially useful is the reaction of the carboxylic acid (II) with the amine (III) in the presence of a dehydrating coupling agent such as dicyclohexylcarbodiimide in a suitable organic solvent such as tetrahydrofuran, dimethylacetamide or dimethylformamide at moderate temperatures, such as room temperature, until reaction is complete usually from 1–12 or more hours.

In the Reaction Sequence A, n, m, R, R$^1$, R$^2$ and R$^3$ are as defined above or are precursor groups on intermediate compounds. The latter may be an ester, ether, nitro or benzyl derivative which generates the desired end or even another intermediate product after regenerative hydrolytic or hydrogenation reactions. The new compounds of Formula II are valuable intermediates and a part of this invention.

The compounds of this invention have pharmacodynamic activity and as such are useful ingredients for pharmaceutical dosage units or methods. More specifically they increase renal blood flow and decrease renal vascular resistance as does dopamine. Their effect in improving kidney function appears to be cumulative. These compounds, therefore, are long acting renal improvement or anti-hypertensive agents.

The biological activity of the compounds of Formula I was demonstrated by administering the compounds by infusion to anesthetized dogs measuring the mean arterial blood pressure, renal blood flow, renal vascular resistance and heart rate in the test procedure explained in detail in U.S. Pat. No. 4,197,297. Generally speaking the compounds gave a decreased renal vascular resistance and/or increased renal blood flow at doses ranging from 1/10 to 1/100 that for dopamine.

One skilled in the art will recognize that the compounds of this invention may exist in various configurations such as optical isomers or mixtures thereof. Such compounds are easily prepared by substituting the desired amino acids of chosen configuration into the chemical reactions of the examples which illustrates this invention. Also the proline ring in the compounds of Formula I may be replaced by other prolyl-like fragments such as dehydroprolyl

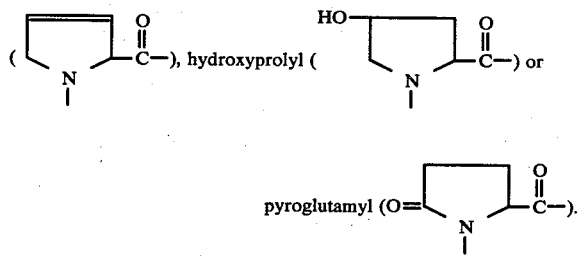

The following examples are intended to teach the preparation and use of the new compounds of this invention but not to limit its scope. All temperatures are expressed in degrees Centigrade.

EXAMPLE 1

A mixture of 4.8 g (0.02 m) of L-proline benzyl ester hydrochloride, 3.88 g (0.02 m) of α-(1-adamantyl)acetic acid, 5.4 g (0.04 m) of 1-hydroxybenzotriazole, 2.56 ml of N-ethylmorpholine, 60 ml of dimethylformamide and 4.16 g (0.02 m) of dicyclohexylcarbodiimide was stirred overnight at 25°. The mixture was filtered and the tetrahydrofuran removed in vacuo from the filtrate to leave a residue which was taken up in 200 ml of ethyl acetate. The resulting extract was acidified with dilute hydrochloride acid. The layers were separated. The organic layer was extracted several times with ethyl acetate. The organic extracts were combined and washed with dilute acid, water, bicarbonate solution and brine then dried and evaporated to give an amber syrup of N-(1-adamantyl)-ethanoylproline benzyl ester, m/e=381. A second run on a 0.04 m scale gave 16.2 g of ester.

This material (16.2 g, 0.043 m) was dissolved in 85 ml of ethyl alcohol and hydrogenated using standard low pressure conditions over 2.5 g of 10% palladium-on-charcoal. The mixture was filtered and the filtrate evaporated to give 7.9 g (64%) of the desired free acid, m.p. 176°-178°, $[\alpha]_D^{25} = -51.3°$ (c 1, methanol).

Anal. Calcd. for $C_{17}H_{25}NO_3$: C, 70.07; H, 8.65; N, 4.61. Found C, 69.99; H, 8.72; N, 4.67.

A mixture of 6.4 g (0.0358 m) of D,L-α-methylphenylalanine, 9.38 g (0.043 m) of di-tert.-butyldicarbonate, 5.0 ml of triethylamine and 100 ml of dimethylformamide was stirred 20 hours at room temperature. The mixture was filtered. The filtrate was evaporated to give a residue which was taken up in ethyl acetate. The extract was washed with water, cold 1 N hydrochloric acid and water. The dried organic extract was evaporated to give a syrup which solidified and was crystallized from hexane-ether, 4.6 g (46%) of N-tert.-butoxycarbonyl-D,L-α-methylphenylalanine, m.p. 134°-135°.

This t.-boc material (4.4 g, 0.016 m) was suspended in dry tetrahydrofuran and reacted with 4.94 g of dicyclohexylcarbodiimide, 4.3 g of ω-nitro-L-arginine, methyl ester hydrochloride, 4.32 g of 1-hydroxybenzothiazole and 2.76 g of N-ethylmorpholine at 0° for 1 hour then at room temperature for 72 hours. Working up as above gave 6.8 g (86%) of N-tert.-butoxycarbonyl-D,L-α-methylphenylalanyl-α-nitro-L-arginine methyl ester, m.p. 143°-145°. $[\alpha]_D^{25}$ (c 1, $CH_3OH$) $= -33.9°$.

Anal. Calcd. for $C_{22}H_{34}N_6O_7$: C, 53.43; H, 6.93; N, 16.99. Found: C, 53.09; H, 6.82; N, 16.61.

This t.-boc 23.0 g (46.6 mm) and 9.2 ml (70 mm) of m-methoxyanisole were suspended in methylene chloride at 0°. After 15 minutes stirring, the mixture was evaporated and ethereal hydrogen chloride added. The separated solid was dissolved in water and washed with ether. The aqueous layer was evaporated under vacuo to give 13.5 g (67%) of D,L-α-methylphenylalanyl-ω-nitro-L-arginine, methyl ester, hydrochloride, $[\alpha]_D^{25}$ (c 1, $H_2O$) $= -32.8°$.

Anal. Calcd. for $C_{17}H_{26}N_6O_5 \cdot HCl \cdot \frac{1}{2}H_2O \cdot \frac{1}{2}C_2H_5OH$: C, 46.70; H, 6.75; N, 18.15. Found: C, 46.32; H, 6.72; N, 18.11.

A mixture of 1.4 g (4.8 mm) of the adamantyl compound and 2.1 g (4.9 mm) of the arginine compound with the coupling reagents mentioned above in stoichiometric quantities in 30 ml of tetrahydrofuran and 5 ml of dimethylformamide was reacted at room temperature for 72 hours. The reaction mixture was filtered and evaporated. The residue was washed as above then passed over a column of 60 g of silica gel using methanol-methylene chloride to give 9 g (28%) of N-(1-adamantyl)-ethanoyl-L-proline-D,L-α-methyl-phenylalanyl-α-nitro-L-arginine methyl ester, $[\alpha]_D^{25} = -78.7°$ (c 0.5, $CH_3OH$).

A mixture of 0.9 g (1.3 mm) of the ester, 15 ml of methanol and 2 ml of 2.5 N sodium hydroxide solution was stirred overnight. The methanol was removed and water added to the residue. Concentrated hydrochloric acid was added slowly to separate 0.8 g (94%) of the free acid.

This material (0.8 g, 1.2 mm) was dissolved in 25 ml of 1:1 ethanol-acetic acid solution then added to a slurry of 1.3 g of palladium-on-barium sulfate in ethanol. After hydrogenation for 6 hours at moderate pressure twice with fresh catalyst, the mixture was filtered. The filtrate was evaporated. The residue was dissolved in methanol and passed over 20 g of silica gel to give 170 mg (23%) of the desired N-(1-adamantyl)-ethanoyl-L-prolyl-D,L-α-methylphenylalanyl-L-arginine hydrate, $[\alpha]_D^{25} = +66.8°$ (c 1, $H_2O$).

Anal. Calcd. for $C_{33}H_{48}N_6O_5.H_2O$: C, 63.24; H, 8.04; N, 13.41. Found: C, 62.95; H, 8.09; N, 13.40.

This compound in the renal vasodilator protocol in anesthetized dogs by infusion gave an $ED_{15}$ of 72 μg/kg., dopamine gave an $ED_{15}$ of 3.5 μg/kg.

Substituting D-proline, benzyl ester hydrochloride in this procedure gives the corresponding isomer.

EXAMPLE 2

The N-acylproline (2.9 g, 0.01 m) from Example 1 is mixed with 2.9 g (0.01 m) of D,L-α-methyl-3,4-dimethoxyphenylalanine methyl ester hydrochloride, 2.7 g (0.02 m) of 1-hydroxybenzotriazole, 2.0 ml of N-ethylmorpholine, 2.06 g (0.01 m) of dicyclohexylcarbodiimide, 20 ml of dimethylformamide and 40 ml of tetrahydrofuran. The mixture is stirred at room temperature for 72 hours.

The reaction mixture is filtered. The filtrate is concentrated. The residue is taken up in ethyl acetate and washed with dilute acid, water, bicarbonate and brine. The organic extract is dried and evaporated to give 5.12 g of N-(1-adamantyl)-ethanoyl-L-prolyl-D,L-α-methyl-3,4-dimethoxyphenylalanine methyl ester.

The ester dipeptide (5.2 g), 45 ml of methyl alcohol and 2.5 ml of 2.5 N sodium hydroxide solution are mixed and stirred for 17 hours. The methanol is taken off and the residue taken up in water and filtered. The aqueous solution is acidified with conc. hydrochloric acid to give a solid which is taken into methylene chloride. After washing with water, the methylene chloride extract is dried and evaporated to give 3.2 g of the desired dipeptide intermediate as the free acid.

Dicyclohexylcarbodiimide (1.28 g, 6.2 mm) is added to a mixture of 3.2 g of the dipeptide acid, 1.67 g of ω-nitro-L-arginine, methyl ester, hydrochloride, 1.68 g of 1-hydroxybenzotriazole, 3.0 ml of N-ethylmorpholine, 10 ml of dimethylformamide and 30 ml of dry tetrahydrofuran. The resulting mixture is stirred at room temperature for 54 hours. The mixture is filtered and the filtrate diluted with iced brine, dilute hydrochloric acid and ethyl acetate. The separated organic extract is washed as above, dried and evaporated to give (1-adamantyl)-ethanoyl-L-prolyl-D,L-α-methyl-3,4-dimethoxyphenylalanyl-ω-nitro-L-arginine methyl ester.

This material (3.7 g) is stirred in 60 ml of methyl alcohol and 20 ml of 2.5 N sodium hydroxide solution at 25° for 17 hours. The alcohol is evaporated off. The residue is suspended in water and filtered. The filtrate is acidified with concentrated hydrochloric acid to give a residue which is dissolved in ethyl acetate-methanol. The extract is washed with brine, dried and evaporated to give the desired acid.

A mixture of 1.8 of this ω-nitro-tripeptide acid, 2.5 g of 10% palladium-on-barium sulfate, 50 ml of ethyl alcohol and 30 ml of glacial acetic acid is hydrogenated at low pressure as described above. The catalyst is removed and the hydrogenation solution is evaporated. The residue is recrystallized to give N-(1-adamantyl)-ethanoyl-L-prolyl-D,L-α-methyl-3,4-dimethoxyphenylalanyl-L-arginine acetic acid salt.

EXAMPLE 3

A mixture of 2.7 g of N-(1-adamantyl)-propionyl-L-prolyl-D,L-α-methyl-3,4-dimethoxyphenylalanine, prepared as described in Example 2, 1.22 g of 1-hydroxybenzotriazole, 1.0 g of N-carbobenzyloxy-1,3-diaminopropane, 4 ml of N-ethylmorpholine, 0.93 g of dicyclohexylcarbodiimide, 30 ml of dry tetrahydrofuran and 10 ml of dimethylformamide is stirred at ambient temperature for 72 hours. The product is isolated as in Example 1 to give the carbobenzoxy dipeptide which is taken over a silica gel column.

This material, 1.6 g, is hydrogenated at low pressure (55 p.s.i.) with 2.0 g of 10% palladium-on-charcoal in 60 ml of ethanol and 20 ml of glacial acetic acid. The filtered mixture is then concentrated. The residue is taken up in ethanol and acidified with ethereal hydrogen chloride to give N-(1-adamantyl)-propionyl-L-prolyl-D,L-α-methyl-3,4-dimethoxyphenylalanine-3-aminopropylamide hydrochloride.

EXAMPLE 4

N-(1-Adamantyl)-ethanoyl-L-proline (2.8 g) is reacted with 2.46 g of D,L-α-methyltyrosine, methyl ester, hydrochloride by the dicyclohexylcarbodiimide route of Example 1 to give N-(1-adamantyl)-ethanoyl-L-prolyl-D,L-α-methyltyrosine, methyl ester. This material (4.9 g) is hydrolyzed in alcoholic alkali to give the desired intermediate acid. This material (4.0 g) is reacted with 2.34 g of ω-nitro-L-arginine, methyl ester, hydrochloride as above to give, after hydrolysis and reduction, N-(1-adamantyl)-propionyl-L-prolyl-D,L-α-methyltyrosyl-L-arginine as the acetic acid salt.

EXAMPLE 5

A mixture of 10 mmoles of N-(1-adamantyl)-butyryl-L-prolyl-D,L-α-methyl-4-methoxyphenylalanine prepared as in Example 2, 10 mm of 3-aminopropylguanidine dihydrobromide (Chem. Abst. 23, 1880), 20 mm of 1-hydroxybenzotriazole, 8 ml of N-ethylmorpholine, 10 mm of dicyclohexylcarbodiimide, 30 ml of dry tetrahydrofuran and 20 ml of dimethylformamide is stirred at 25° for 18 hours. After filtration, the filtrate is evaporated. The residue is dissolved in ethyl acetate. The extract is washed with 3% aqueous acetic acid, water and 5% sodium bicarbonate solution. The dried concentrated residue is dissolved in methyl alcohol and added dropwise to 5:1 ether-petroleum ether to give N-(1-adamantyl)-butyryl-L-prolyl-D,L-α-methyl-4-methoxyphenylalanine 3-guanidinopropylamide as an amorphous solid.

N-(1-Adamantyl)-ethanoyl-prolyl-D,L-α-ethyl-4-methoxyphenylalanine-3-guanidinopropylamide is prepared in like fashion. Also using the condensation method of Example 3 but substituting a stoichiometric quantity of methyl ω-aminocaproate to give the methyl ester derivative of the peptide followed by saponification using sodium hydroxide-methanol as in Example 2 gives N-(1-adamantyl)-propionyl-L-prolyl-D,L-α-methyl-3,4-dimethoxyphenylalanine-ω-carboxypentylamide.

The new chemical compounds described above are incorporated into dosage unit forms and used in methods for improving renal function, treating high blood pressure or treating shock using standard methods as disclosed in the above referenced U.S. Pat. No. 4,197,297 at line 19 column 6 to line 48 column 7 as well as Examples 8 and 9. The doses of the present compounds in the pharmaceutical dosage unit will be an effective nontoxic quantity selected from 50–500 mg of active base, preferably 75–250 mg. These are administered to patients in need of treatment for the noted clinical conditions from 1–5 times daily.

What is claimed is:

1. A chemical compound of the structural formula:

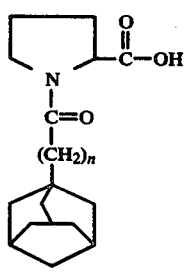
in which n is an integer of 1-3.
2. The chemical compound of claim 1 being N-(1-adamantyl)-ethanoylproline.
* * * * *
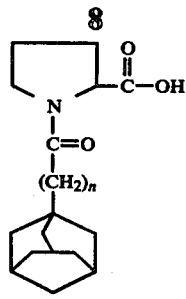
in which n is an integer of 1-3.
2. The chemical compound of claim 1 being N-(1-adamantyl)-ethanoylproline.
* * * * *